United States Patent [19]

Huss et al.

[11] Patent Number: 4,968,306
[45] Date of Patent: Nov. 6, 1990

[54] INTRAVASCULAR CATHETER HAVING AN ADJUSTABLE LENGTH INFUSION SECTION TO DELIVERY THERAPEUTIC FLUID

[75] Inventors: Beverly A. Huss, Santa Clara; Robert W. Reinhardt, San Jose, both of Calif.

[73] Assignee: Advanced Cardiovascular Systems, Inc., Santa Clara, Calif.

[21] Appl. No.: 377,243

[22] Filed: Jul. 7, 1989

[51] Int. Cl.$^5$ ............................................. A61M 5/325
[52] U.S. Cl. ..................................... 604/264; 604/275
[58] Field of Search .............. 604/264, 158, 164, 165, 604/272, 273, 274, 275, 280

[56] References Cited

U.S. PATENT DOCUMENTS

| 3,860,006 | 1/1975 | Patel | 604/164 |
| 4,149,535 | 4/1979 | Volder | 604/164 X |
| 4,493,696 | 1/1985 | Uldall | 604/164 |
| 4,702,260 | 10/1987 | Wang | 604/264 |

Primary Examiner—John D. Yasko
Attorney, Agent, or Firm—Fulwider, Patton, Lee & Utecht

[57] ABSTRACT

An elongated catheter assembly for the intravascular delivery of therapeutic fluids which has an infusion section on the distal end for the discharge of fluids to the exterior of the catheter and an elongated sheath which moves longitudinally to vary the length of the infusion section through which treatment fluid can pass. The sheath preferably is elongated so that the position thereof can be adjusted from the proximal end of the catheter assembly. In this manner, the effective length of the infusion section can be adjusted to the length of the treatment site, such as a thrombus.

12 Claims, 2 Drawing Sheets

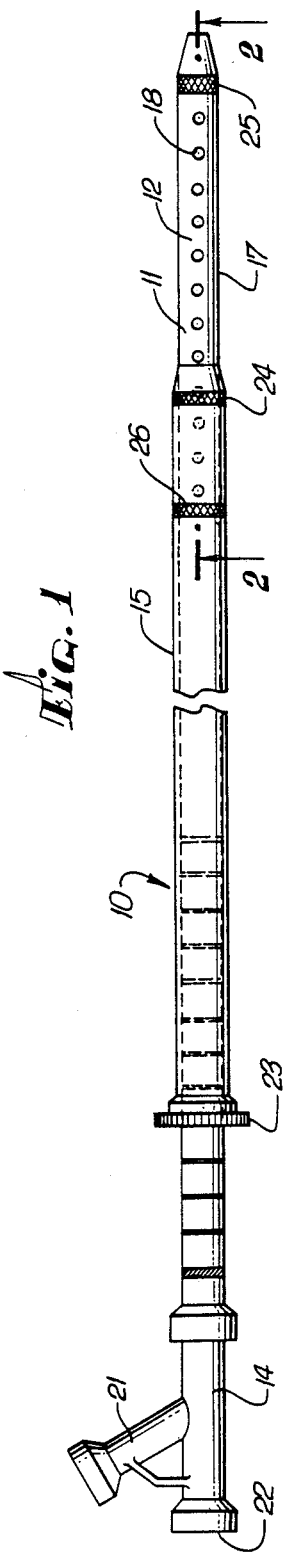
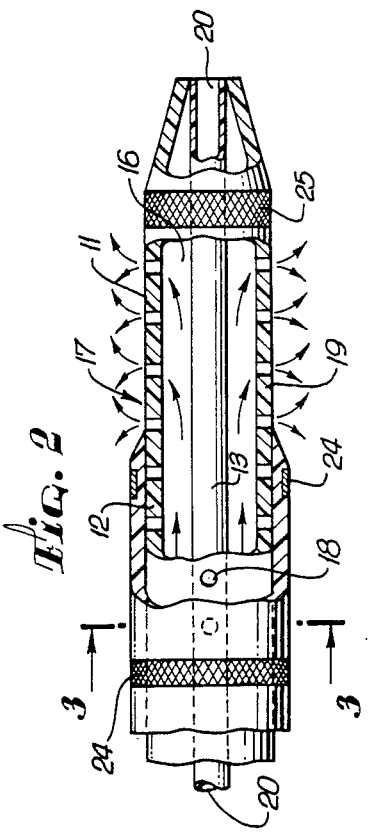
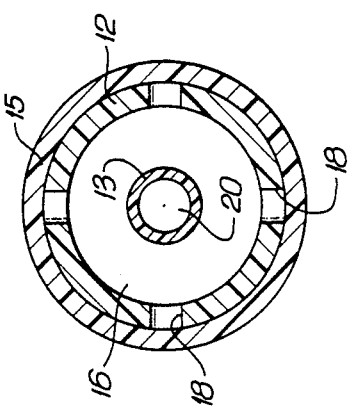

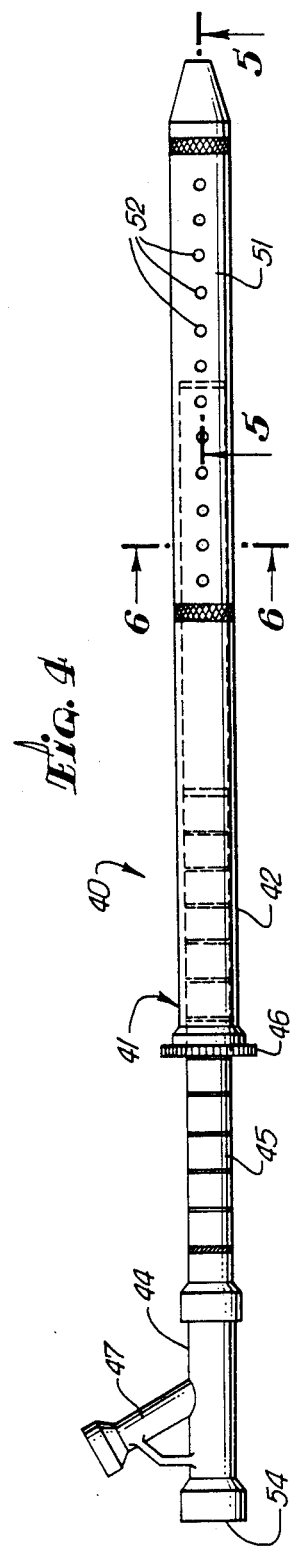
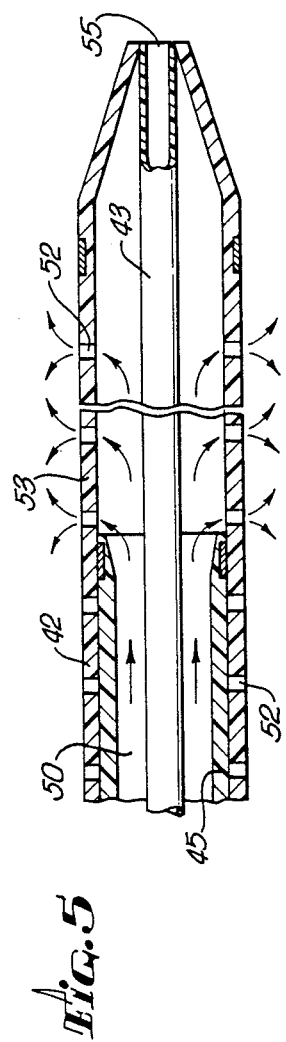
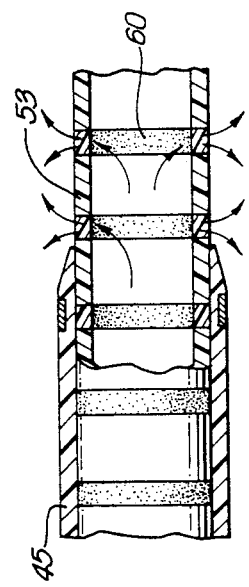
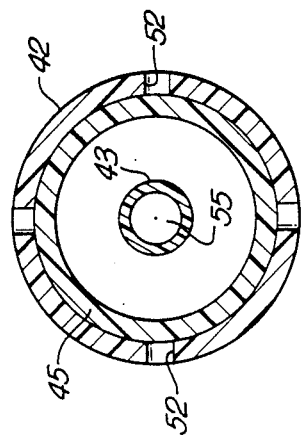

INTRAVASCULAR CATHETER HAVING AN ADJUSTABLE LENGTH INFUSION SECTION TO DELIVERY THERAPEUTIC FLUID

BACKGROUND OF THE INVENTION

This invention generally relates to a vascular catheter which delivers therapeutic fluid to a desired location within a patient's vasculature.

Therapeutic fluids such as those containing urokinase, streptokinase, tissue plasminogen activator (TPA) have been found effective in many instances in the treatment of vascular thrombosis. The systemic administration of such therapeutic agents is not always desirable because the entire body of the patient must be medicated in order to treat small vascular sites. Delivery of therapeutic fluids through vascular catheters directly to a desired treatment site is usually more effective and, moreover, with direct delivery higher concentrations of the therapeutic agent may be used in the treating solution.

In the direct delivery of therapeutic fluid to a thrombotic region in the patient's vasculature, it is highly desirable to limit the application of the therapeutic fluid only to the treatment site to limit the amount of therapeutic agent used (which can be very expensive) and to avoid over medicating the patient. Frequently, there are multiple treatment sites of various lengths which require the use of multiple catheters having at the distal end thereof drug delivery sections of various lengths to effectively deliver the treatment fluid only to the treatment site. In these instances, either a separate catheter must be used at each treatment site, which increases the time and the inconvenience of the procedure, or inefficient application of the treatment fluid must be accepted.

What has been needed is a catheter delivery system which can deliver therapeutic fluids to one or more thrombotic sites with means to adjust the effective length of drug delivery section of the catheter body, particularly after the catheter has been inserted into the patient's blood vessels. The present invention provides a catheter which satisfies this need.

SUMMARY OF THE INVENTION

The present invention is directed to a catheter for the intravascular delivery of drugs or therapeutic agents wherein the effective length of the catheter section which delivers the treatment fluid can be adjusted after the catheter is inserted into the patient's vascular system.

The catheter assembly in accordance with the invention has an elongated catheter body with an inner lumen which extends from the proximal end thereof to an infusion section in the distal portion thereof having passageways in the wall thereof for discharging fluid from the lumen. Longitudinally movable means such as a sheath is provided to adjust the effective length of the infusion section.

In one presently preferred embodiment, a snugly fitting sheath is slidably mounted onto the exterior of the catheter body so that longitudinal or axial movement of the sheath with respect to the catheter body blocks or unblocks a greater or lesser number of fluid flow passageways in the wall of the infusion section. In another presently preferred embodiment, a tubular sheath snugly fits within the interior of the catheter body and is adapted to be slidable therein so that a greater or lesser number of fluid flow passageways passing through the wall of the infusion section are blocked or unblocked to thereby control the effective length of the infusion section.

The elongated catheter body generally has an outer tubular element and an inner tubular element coaxially disposed within the outer tubular element with the distal ends of these tubular members sealingly bonded together to prevent loss of therapeutic fluids therefrom. An annular lumen which is defined between the inner and outer tubular element directs therapeutic fluids from an adapter provided on the proximal end of the catheter body to the distal portion thereof having the infusion section. The length of the infusion section in the distal portion of the catheter which is effective in infusing therapeutic fluid may be adjusted prior to or after inserting the catheter into a patient's vascular system. These adjustments are performed from the proximal end of the catheter which normally extends out of the patient during the vascular procedure.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view partially in section of a drug delivery catheter embodying features of the invention;

FIG. 2 is an enlaged view of the distal end of the catheter shown in FIG. 1 partially in section;

FIG. 3 is a transverse cross-sectional view of the catheter shown in FIG. 1 taken along the lines 2-2;

FIG. 4 is an elevational view of another drug delivery catheter embodying features of the invention;

FIG. 5 is an enlarged sectional view of the distal end of the catheter shown in FIG. 4 taken along the lines 5—5 shown in FIG. 4

FIG. 6 is a cross-sectional view of the drug delivery catheter shown in FIG. 4 taken along the lines 6—6; and FIG. 7 is a partial longitudinal view in section of a distal section of a drug delivery system similar to that shown in FIG. 1 with a porous section to discharge fluid through the wall of the catheter.

DETAILED DESCRIPTION OF THE INVENTION

Reference is made to FIGS. 1-3 which illustrate a catheter assembly for the intravascular delivery of therapeutic fluids. The catheter assembly 10 generally includes an elongated catheter body 11 having an outer tubular element 12 and an inner tubular element 13 concentrically disposed therein, an adapter 14 on the proximal end of the catheter body, and an elongated sheath 15 mounted for slidable movement on the exterior of the catheter body 11.

The inner and outer tubular elements 13 and 12, respectively, define therebetween an annular lumen 16 for directing treatment fluid to the infusion section 17 in the distal portion of the catheter body 11 wherein fluid flow passageways 18 provided in the wall 19 of the outer tubular element 12. The distal ends of the inner and outer tubular elements 13 and 12 are sealingly bonded such as by adhesive, heat shrinking, or other suitable means to prevent loss of the treatment fluid therefrom. The inner tubular element 13 is provided with an inner lumen 20 adapted to receive a guidewire (not shown)

which facilitates advancing the catheter to the desired vascular site.

The adapter 14 has a side arm 21 which directs therapeutic fluid to the annular lumen 16 in the catheter body 11. A guidewire would extend through the proximal end 22 of the adapter into the inner lumen 20.

The outer elongated tubular sheath 15 is mounted about the outer tubular element 12 for slidable longitudinal movement thereon. The distal end of the sheath 15 fits the outer tubular element 12 snugly so as to effectively prevent discharge fluid through the blocked passageways. A tightenable collar 23 is provided on the sheath 15 to fix the relative longitudinal position of the sheath with respect to the outer tubular element. It also seals the proximal end of the sheath to prevent leakage of treatment fluid therefrom. Radiopaque marker 24 is provided on the distal end of the sheath 15 and radiopaque markers 25 and 26 are provided on the proximal and distal ends of the infusion section 17 to be able to fluoroscopically visualize these components when the catheter is inserted into the patient's vasculature.

The passageways or ports 18 are provided through the wall of the distal portion of the outer tubular element 12 between the two markers 25 and 26 to infuse therapeutic fluids at a desired vascular site. The length of the infusion section 17 which is effective in discharging fluid is varied by changing the relative longitudinal position of the distal end of the sheath 15 thereon to accommodate thrombi of various lengths.

In utilizing the invention, the catheter assembly 10 is introduced into the patient's vascular system percutaneously through a guiding catheter with a guidewire slidably disposed within the inner lumen 20 of the inner tubular element 12. Once the infusion section 17 is properly positioned within a desired location, the length thereof which is exposed is adjusted by axial movement of the sheath 15 at the proximal end thereof which extends out of the patient. The effective length of the infusion section 17 is preferably the approximate length of the thrombus site to be treated. Other treatment sites of different lengths can also be subsequently treated by readjusting the effective length of the infusion section in essentially the same manner.

FIGS. 4–6 illustrate an alternative catheter assembly 40 which is similar in many respects to the catheter assembly shown in FIGS. 1, 2 and 3. In this embodiment, the catheter body 41 has inner and outer tubular elements 42 and 43 Tubular sheath 45 is slidably mounted within the interior of the tubular element 42 and an adapter 44 provided on the proximal end thereof. The proximal end of the outer tubular element 42 is provided with a tightenable collar 46 which sealingly engages the exterior of the sheath 45 and thereby fixes the relative position between the sheath 45 and the outer tubular element 42.

The proximal ends of the sheath 45 and the inner tubular member 43 are secured to the adapter 44. The side arm 47 of adapter 44 directs treatment fluid through the annular passageway 50 disposed between the inner tubular member 43 and the sheath 45 and/or the outer tubular member 42 to the infusion section 51. The infusion section 51 is provided with fluid flow passageways 52 for infusing treatment fluid through wall 53 in the outer tubular element 42 to the exterior of the catheter body 41. A guidewire (not shown) extends through the proximal end 54 of the adapter 44 into the inner lumen 55 provided in inner tubular element 43.

The embodiment shown in FIGS. 3, 4 and 5 operates in a similar manner as the catheter assembly shown in FIGS. 1 and 2 except that the proximal end of the outer tubular element 42 is secured to the exterior of the sheath 45 by means of the collar 46 to fix the relative position therebetween. As the outer tubular element 42 is moved longitudinally over the sheath 45, a greater or lesser number of infusion ports 52 are opened thereby adjusting the effective length of the infusion section 51.

As shown in FIG. 7, the fluid flow passageways 18 and 52 of the prior embodiments may be replaced by porous sections 60 formed of suitable plastic material which allows the passage of the treatment fluid from the annular lumen 51 to the exterior of the catheter. Indeed, the entire infusion section can be formed from a porous plastic material.

The sheath and the inner and outer tubular elements of the catheter body may be formed from suitable plastic materials, such as polyethylene, polyimide and polyesters such as Hytrel 7246, which is a block copolymer of polybutylene terephthalate and long chain polyester glycols. Hytrel is a trademark of the DuPont Company. Porous plastic materials for fluid discharge may be formed from polypropylene.

In the embodiment shown in FIGS. 1–3, the sheath 15 is typically about 90 cm in length with an inner diameter of about 0.059 inch and an outer diameter of about 0.065 inch. The outer tubular element 12 of this embodiment has a length of about 130 cm with an inner diameter of about 0.051 and an outer diameter of about 0.059 and the inner tubular element 13 has a length of about 130 cm, an inner diameter of about 0.040 inch, and an outer diameter of about 0.047 inch. In the embodiment shown in FIGS. 3, 4 and 5, typically the sheath 45 is about 90 cm in length with an inner diameter of about 0.051 and an outer diameter of about 0.055. The outer tubular element 42 has a length of about 90 cm with an inner diameter of about 0.055 inch and an outer diameter of about 0.063 inch, and the inner tubular element 43 has a length of about 120 cm, an inner diameter of about 0.040 inch, and an outer diameter of about 0.047 inch. The dimensions of the components may vary widely, depending upon the vascular use of the catheter.

The infusion sections 17 and 51 are about 10–30 cm in length, typically about 20, cm with about 30 passageways provided in the wall of the outer members 12 and 42 with effective diameters of about 0.005 inch. Preferably the passageways are aligned along the length of the outer tubular element in 3 spirals of 10 passageways each. If porous plastic materials are employed for fluid discharge, it should have an effective pore size of about 2 to about 20 microns.

The number and effective size of the passageways or porous sections will be determined to a large extent upon the desired flow rate of therapeutic fluids and the pressure thereof in the annular lumen between the inner and outer tubular members which form the catheter body. The typical values given above were designed for a flow rate of about 80 cc's per hour at a pressure of about 3 to 10 psi. Other flow rates and pressures may require a different number of passageways and different passageway diameters.

Various modifications and improvements can be made to the present invention. For example, in the preferred embodiments described herein, a single annular lumen is employed to direct treatment fluid to the entire infusion section. However, in order to provide a more uniform delivery of the treatment fluid, the annular lumen may be compartmentalized as described and claimed in copending application Ser. No. 295,088, filed Jan. 9, 1989 (Dake et al.) which is hereby incorporated by reference in its entirety. In this modification, each compartment of the annular lumen will supply fluid to a particular set of passageways. Preferably, such lumen compartment has a separate source of treatment fluid. Other modifications and improvements can be made without departing from the scope of the invention.

What is claimed is:

1. A catheter for the intravascular delivery of therapeutic fluid, comprising:
   (a) an elongated catheter body having inner and outer tubular members which have distal ends sealingly secured together an annular lumen extending between the inner and outer tubular members to direct therapeutic fluid from the proximal end thereof to a fluid infusion section in a distal portion of the outer tubular member and means to pass therapeutic fluid from the annular lumen through the wall of the infusion section in the outer tubular member to the exterior of the catheter;
   (b) an adapter on the proximal end of the catheter body for directing therapeutic fluids from a source thereof of the annular lumen in the catheter body; and
   (c) means longitudinally movable with respect to the distal portion of the catheter body to adjust the effective length of the infusion section thereof.

2. The catheter of claim 1 wherein the means to pass fluid through the wall of the infusion section is a plurality of passageways.

3. The catheter of claim 2 wherein the passageways have an effective diameter of about 0.002 to about 0.01 inch.

4. The catheter of claim 3 wherein there are about 20 to about 40 passageways in the infusion section.

5. The catheter of claim 4 wherein the passageways through the wall of the infusion section are disposed spirally along the length of the infusion section.

6. The catheter of claim 5 wherein the passageways extend about one complete revolution about the catheter body.

7. The catheter of claim 6 wherein there are a plurality of spiral lines of passageways.

8. The catheter of claim 1 wherein the means to adjust the effective length of the infusion section is a sheath, the longitudinal movement of which closes or opens fluid flow passageways in the wall of the infusion section.

9. The catheter of claim 1 wherein the means to pass fluid through the wall of the infusion section comprises porous plastic material.

10. The catheter of claim wherein the catheter body comprises an outer tubular element an inner tubular element concentrically disposed therein which defines therebetween an annular lumen for directing therapeutic fluid to the infusion section.

11. The catheter of claim 8 wherein the catheter body comprises an outer tubular element and an inner tubular member concentrically disposed therein and wherein the sheath is disposed on the inner surface of the outer tubular element.

12. The catheter of claim 12 wherein the outer tubular member has on the proximal end thereof means to sealingly engage the exterior of the sheath.

* * * * *

UNITED STATES PATENT AND TRADEMARK OFFICE
CERTIFICATE OF CORRECTION

PATENT NO. : 4,968,306
DATED : November 6, 1990
INVENTOR(S) : Beverly A. Huss and Robert W. Reinhardt It is certified that error appears in the above-identified patent and that said Letters Patent is hereby corrected as shown below:

Column 2, line 41: "FIG. 4" should be -- FIG. 3 --.

Column 3, line 49: Following "43" insert -- . --.

Column 3, line 50: Following "the" (second occurence) insert -- outer --.

Column 5, line 27: "of" should be -- to --.

Column 6, line 22: Following "claim" insert -- 8 --.

Column 6, line 32: "claim 12" should be -- claim 11 --.

Signed and Sealed this

Twenty-third Day of June, 1992

Attest:

DOUGLAS B. COMER

*Attesting Officer*          *Acting Commissioner of Patents and Trademarks*